(12) United States Patent
Winkler

(10) Patent No.: US 8,063,246 B2
(45) Date of Patent: Nov. 22, 2011

(54) METHOD FOR PURIFYING FLUE GASES FROM COMBUSTION PLANTS AND THEN PRODUCING UREA

(75) Inventor: Hermann Winkler, Recklinghausen (DE)

(73) Assignee: Evonik Energy Services GmbH, Essen (DE)

( * ) Notice: Subject to any disclaimer, the term of this patent is extended or adjusted under 35 U.S.C. 154(b) by 233 days.

(21) Appl. No.: 12/451,104

(22) PCT Filed: Apr. 18, 2008

(86) PCT No.: PCT/EP2008/003129
§ 371 (c)(1),
(2), (4) Date: Oct. 26, 2009

(87) PCT Pub. No.: WO2008/135150
PCT Pub. Date: Nov. 13, 2008

(65) Prior Publication Data
US 2010/0099914 A1    Apr. 22, 2010

(30) Foreign Application Priority Data
May 2, 2007  (DE) .................. 10 2007 020 855

(51) Int. Cl.
C07C 273/04   (2006.01)
(52) U.S. Cl. ............... 564/67; 564/70; 564/71; 564/72; 423/220
(58) Field of Classification Search ........... 564/67, 564/70, 71, 72; 423/220
See application file for complete search history.

(56) References Cited

U.S. PATENT DOCUMENTS

| | | | |
|---|---|---|---|
| 3,037,844 A | 6/1962 | Giammarco | 23/150 |
| 3,674,707 A | 7/1972 | Pieters et al. | 502/26 |
| 4,407,733 A | 10/1983 | Birkenstock et al. | 502/174 |
| 4,434,144 A | 2/1984 | Giammarco et al. | 423/223 |
| 4,615,991 A | 10/1986 | Obayashi et al. | 502/28 |
| 4,656,147 A | 4/1987 | Iida et al. | 502/26 |
| 4,764,498 A | 8/1988 | Wissner et al. | 502/251 |
| 5,120,690 A | 6/1992 | Jung et al. | 501/155 |
| 5,151,256 A | 9/1992 | Kato et al. | 423/210 |
| 5,283,052 A | 2/1994 | Hums | 422/223 |
| 5,394,610 A | 3/1995 | Stoephasius et al. | 29/890 |
| 5,522,941 A | 6/1996 | Uchinami et al. | 134/37 |
| 5,571,771 A | 11/1996 | Abel et al. | 502/330 |
| 5,785,937 A | 7/1998 | Neufert et al. | 423/213.2 |
| 5,811,066 A | 9/1998 | Winkler et al. | 423/210 |
| 5,820,693 A | 10/1998 | Patchett et al. | 134/22.12 |
| 5,832,712 A | 11/1998 | Rønning et al. | 60/39.02 |
| 5,869,419 A | 2/1999 | Obayashi et al. | 502/305 |
| 5,873,329 A | 2/1999 | Heering et al. | 122/7 R |
| 5,882,422 A | 3/1999 | Obayashi et al. | 134/1 |
| 5,953,911 A | 9/1999 | Guth et al. | 60/295 |
| 6,025,292 A | 2/2000 | Obayashi et al. | 502/27 |
| 6,080,696 A | 6/2000 | Duke et al. | 502/27 |
| 6,136,222 A | 10/2000 | Friesen et al. | 252/184 |
| 6,232,254 B1 | 5/2001 | Schneider et al. | 502/22 |
| 6,241,286 B1 | 6/2001 | Ogura et al. | 281/29 |
| 6,241,826 B1 | 6/2001 | Dittmer et al. | 134/1 |
| 6,299,695 B1 | 10/2001 | Gilgen | 134/1 |
| 6,387,836 B1 | 5/2002 | Dorr et al. | 502/22 |
| 6,395,665 B2 | 5/2002 | Nojima et al. | 502/25 |
| 6,455,456 B1 | 9/2002 | Spokoyny | 502/20 |
| 6,482,762 B1 | 11/2002 | Ruffin et al. | 502/33 |
| 6,484,733 B2 | 11/2002 | Budin et al. | 134/22.19 |
| 6,576,585 B2 | 6/2003 | Fischer et al. | 502/309 |
| 6,579,507 B2 | 6/2003 | Pahlman et al. | 423/210 |
| 6,596,248 B2 | 7/2003 | Schimkat et al. | 423/220 |
| 6,596,661 B2 | 7/2003 | Neufert | 502/28 |
| 6,610,263 B2 | 8/2003 | Pahlman et al. | 423/239.1 |
| 6,631,727 B2 | 10/2003 | Schneider et al. | 134/110 |
| 6,641,785 B1 | 11/2003 | Neufert et al. | 422/177 |
| 6,913,026 B2 | 7/2005 | Winnestaffer et al. | 134/22.18 |
| 6,929,701 B1 | 8/2005 | Patel et al. | 134/1 |
| 7,255,842 B1 | 8/2007 | Yeh et al. | 423/234 |
| 7,384,882 B2 | 6/2008 | Sun et al. | 502/27 |
| 7,569,506 B2 | 8/2009 | Foerster | 502/27 |
| 2001/0006929 A1 | 7/2001 | Budin et al. | 502/24 |
| 2002/0006860 A1 | 1/2002 | Schneider et al. | 502/22 |
| 2004/0137209 A1 | 7/2004 | Zeller et al. | 428/304.4 |
| 2004/0163676 A1 | 8/2004 | Winnestaffer et al. | 134/17 |
| 2005/0119109 A1 | 6/2005 | Schneider et al. | 502/22 |
| 2006/0060219 A1 | 3/2006 | Rabitsch et al. | 134/22.11 |

(Continued)

FOREIGN PATENT DOCUMENTS

CA    2336562    1/2000
(Continued)

OTHER PUBLICATIONS

Emissions Control, *SCR Maintenance Fundamentals*, Ken Wicker and Jim Staudt, POWER, Jun. 2004, pp. 52-57.

(Continued)

*Primary Examiner* — Pete O Sullivan
(74) *Attorney, Agent, or Firm* — K&L Gates, LLP

(57) ABSTRACT

A method and apparatus is provided for cleaning flue gases from combustion plants. The method includes removing dust and removing nitrogen from flue gases, bringing flue gases into contact with an aqueous ammonia solution in the presence of an oxidizing agent whereby a reaction solution forms which contains at least ammonium carbonate, heating the reaction solution such that ammonium carbonate decomposes and carbon dioxide and ammonia transfer into the gas atmosphere, and reacting the gaseous carbon dioxide and the gaseous ammonia to form urea. The apparatus includes a device for removing nitrogen and removing dust from the flue gases, a washing device downstream of the device for removing nitrogen and removing dust, a stripper downstream of the washing device, and a urea installation downstream of the stripper.

7 Claims, 1 Drawing Sheet

U.S. PATENT DOCUMENTS

| | | | |
|---|---|---|---|
| 2006/0094587 A1 | 5/2006 | Lee et al. | 502/27 |
| 2006/0135347 A1 | 6/2006 | Schluttig et al. | 502/25 |
| 2006/0148639 A1 | 7/2006 | Foerster | 502/27 |
| 2007/0016150 A1 | 1/2007 | Blohm et al. | 705/37 |
| 2007/0032373 A1 | 2/2007 | Matsumoto et al. | 502/20 |
| 2008/0072762 A1 | 3/2008 | Gal | 96/242 |
| 2008/0115800 A1 | 5/2008 | Blohm | 134/1 |
| 2009/0162708 A1 | 6/2009 | Zhu et al. | 429/17 |
| 2009/0233786 A1 | 9/2009 | Hartenstein et al. | 502/25 |
| 2009/0233787 A1 | 9/2009 | Hartenstein et al. | 502/25 |

FOREIGN PATENT DOCUMENTS

| | | |
|---|---|---|
| DE | 2 015 156 | 10/1971 |
| DE | 38 10 137 A1 | 10/1989 |
| DE | 38 16 600 A1 | 11/1989 |
| DE | 40 13 720 | 10/1991 |
| DE | 42 17 738 | 12/1993 |
| DE | 43 00 933 C1 | 5/1994 |
| DE | 195 33 912 A1 | 3/1997 |
| DE | 196 28 212 A1 | 1/1998 |
| DE | 197 23 796 | 12/1998 |
| DE | 198 04 522 | 2/1999 |
| DE | 198 29 916 A1 | 1/2000 |
| DE | 102 18 380 A1 | 11/2003 |
| DE | 102 22 915 A1 | 1/2004 |
| DE | 102 41 004 A1 | 3/2004 |
| DE | 102 42 081 A1 | 3/2004 |
| DE | 103 25 779 A1 | 1/2005 |
| EP | 0 335 240 A2 | 3/1989 |
| EP | 0 353 467 A1 | 2/1990 |
| EP | 0 571 664 | 12/1993 |
| EP | 0 677 320 | 10/1995 |
| EP | 0 763 589 B1 | 3/1997 |
| EP | 0 792 186 | 9/1997 |
| EP | 0 824 973 A2 | 2/1998 |
| EP | 0 910 472 B1 | 4/1999 |
| EP | 19990936166 | 7/1999 |
| EP | 1 098 703 | 5/2001 |
| EP | 1107 824 | 6/2001 |
| EP | 1 797 954 | 6/2007 |
| EP | 1 833 606 | 9/2007 |
| GB | 1 287 548 | 3/1970 |
| GB | 1283737 | 8/1972 |
| JP | 56037048 | 4/1981 |
| JP | 58 30345 | 2/1983 |
| JP | 2007-297248 | 11/2007 |
| WO | WO 95/20434 | 8/1995 |
| WO | WO 98/02248 | 1/1998 |
| WO | WO 98/55230 | 12/1998 |
| WO | WO 00/01483 | 1/2000 |
| WO | WO 00/12211 | 3/2000 |
| WO | WO 03/099437 A1 | 12/2003 |
| WO | WO 2004/022226 A1 | 3/2004 |
| WO | WO 2004/026447 A1 | 4/2004 |
| WO | WO 2004/073835 A1 | 9/2004 |
| WO | WO 2004/076067 A1 | 9/2004 |
| WO | WO 2006/022885 A1 | 3/2006 |
| WO | WO 2006/072569 | 7/2006 |

OTHER PUBLICATIONS

*The Role of Oxalate in Accelerating the Reductive Dissolution of Hematite ($\alpha$-$FE_2O_3$) by Ascorbate*, Steven Banwart, Simon Davies, and Werner Stumm, Colloids and Surfaces, vol. 39, pp. 303-309 (1989).

*Regeneration of Commercial $TiO_2$-$V_2O_5$-$WO_3$ SCR Catalysts Used in Bio Fuel Plants*, Raziyeh Khodayari and C.U. Ingemar Odenbrand, Appliwed Catalysis B. Environmental, vol. 30, pp. 87-99 (2001).

*Differenzierung der Eisenoixde des Bodens durch Extraktion mit Ammoniumoxalat-Losung*, Dr. Von U. Schwertmann May 3, 1964, pp. 194-202.

Wypych, George Knovel Solvents—A Properties Database. Acetic Acid. ChemTec Publishing. Copyright 2008. Online version available at http://knvel.com/web/portal/browse/display?_EXT_KNOVEL_DISPLAY_bookid=635&verticalID=0, (2008).

Wypych, George Knovel Solvents—A Properties Database. Formic Acid. ChemTec Publishing. Copyright 2008. Online version available at http://knvel.com/web/portal/browse/display?_EXT_KNOVEL_DISPLAY_bookid=635&verticalID=0, (2008).

*Textbook of Inorganic Chemistry*, Holleman—Wiberg, revised by Nils Wiberg, $102^{nd}$ edition, Walter de Gruyter, Berlin—New York, 2007, pp. 671-672, with translation.

U.S. Appl. No. 11/640,475, filed Dec. 15, 2006, Brüggendick, et al.
U.S. Appl. No. 12/287,347, filed Oct. 8, 2008, Hartenstein, et al.
U.S. Appl. No. 12/287,365, filed Oct. 8, 2008, Hartenstein, et al.
U.S. Appl. No. 12/082,761, filed Apr. 14, 2008, Winkler.
U.S. Appl. No. 12/384,159, filed Apr. 1, 2009, Bruggendick, et al.

METHOD FOR PURIFYING FLUE GASES FROM COMBUSTION PLANTS AND THEN PRODUCING UREA

CROSS-REFERENCE TO RELATED APPLICATIONS

This application claims the benefit of PCT International Application, PCT/EP2008/003129, filed Apr. 18, 2008, claiming priority from German application DE 10 2007 020 855.5, filed May 2, 2007. The disclosures of which are incorporated herein by reference.

FIELD OF THE INVENTION

The present invention relates to a method of cleaning flue gases from combustion plants, particularly power stations, and to an apparatus for carrying out this method. The present invention relates in particular to a method and an apparatus for removing carbon dioxide from such flue gases.

BACKGROUND OF THE INVENTION

Exhaust gases from combustion plants, so-called flue gases, include a number of contaminants which must be removed from them in accordance with the current environmental regulations. Some of the contaminants to be removed include, for instance, sulfur oxides, nitrogen oxides and inorganic fluorine and chlorine compounds. New combustion plants are therefore equipped with flue gas cleaning devices, which remove the sulfur oxides, nitrogen oxides and inorganic fluorine and chlorine compounds from them. The flue gases are commonly also conducted through a series of filters in order to remove ash particles from the flue gases.

There is increased focus to remove a portion of the carbon dioxide from the flue gases since carbon dioxide is a so-called greenhouse gas, which is partially responsible for the so-called greenhouse effect. One approach to reducing the $CO_2$ emission is to remove it from the flue gas flow and to store it deep in the earth or beneath the sea bed. This approach has, however, the disadvantage that there is no guarantee that the carbon dioxide thus stored will not be liberated again as a result of tectonic movement. This approach also has the disadvantage that extremely high costs are associated with it, on the one hand for the location of suitable storage sites and on the other hand for the actual insertion into the storage sites. The high costs associated with known methods for reducing the $CO_2$ emissions prevent wide usage of this method or make it more difficult.

SUMMARY OF THE INVENTION

It is therefore an object of the invention to provide an alternative, economical method for removing carbon dioxide from flue gases and an apparatus suitable therefore.

The present invention provides a method of cleaning flue gases from combustion plants with the subsequent production of urea.

In a first method step, dust and nitrogen are removed from the flue gases, whereby the sequence of these two cleaning steps is not of importance to the invention. The removal of dust in the context of this invention includes the removal of fine ash, which is also referred to as dust, and the removal of coarse ash from the flue gases. Numerous methods and devices for removing dust or ash from flue gases are known from the prior art. These include centrifugal separators, filtration separators, electrostatic precipitators and wet scrubbers. The present invention is not limited to one of the aforementioned separation methods—depending on the field of application of the method in accordance with the invention any desired method can be used for the removal of dust.

In order to remove nitrogen from the flue gases, any method known from the prior art for $NO_x$ separation can be used. Methods usable in the context of this invention may be grouped as follows: a) selective, non-catalytic reduction (SNCR), b) selective catalytic reduction (SCR), and c) different dry $NO_x$ separation methods (e.g. electron beam methods (EBM)).

In a subsequent treatment step, at least a portion of the flue gases is brought into contact with an aqueous ammonia solution in the presence of an oxidizing agent. When this contact process occurs, the carbon dioxide from the flue gas reacts with the ammonia in the solution to form ammonium carbonate, whereby a reaction solution forms, in which ammonium carbonate is present in dissolved form. The flue gases also contain sulfur dioxide, which react, when the flue gases are brought into contact with the aqueous ammonia solution, in the presence of an oxidizing agent to form ammonium sulfate and is present after its formation in the reaction solution in dissolved form. Atmospheric oxygen is commonly used as the oxidizing agent but other oxidizing agents can, however, also be used in the context of this invention. In the event that the flue gases do not contain a sufficiently high concentration of oxygen in order to ensure oxidation of the sulfur dioxide, additional oxidizing agent can be supplied, that is to say, for instance, directly into the flue gases before entry into the washing device or whilst they are brought into contact with the ammonia solution.

When the flue gases are brought into contact with the aqueous ammonia solution, the concentration of two gases in the flue gases is thus successfully reduced, namely the concentration of carbon dioxide and the concentration of sulfur dioxide. The contact process itself can, for instance, be effected by injection of the aqueous ammonia solution. However, depending on the flow rate, numerous other variants known to the expert are also possible.

After bringing the flue gases into contact with the aqueous ammonia solution, the reaction solution thus produced is so heated in a suitable device that the ammonium carbonate contained in the reaction solution decomposes and carbon dioxide and ammonia transfer into the gas phase but the ammonium sulfate remains in the reaction solution in an un-decomposed state. For this purpose, the reaction solution is heated under normal pressure to more than 58° C., the decomposition of ammonium carbonate begins at this temperature. In order to accelerate the decomposition, it is possible to perform the decomposition under a reduced pressure or in the presence of an appropriate catalyst.

It is thus possible with this method step to remove carbon dioxide in a targeted manner from the reaction solution which has previously been extracted from the flue gases by conversion to ammonium carbonate. After the heating process, the reaction solution contains primarily dissolved ammonium sulfate. The carbon dioxide and ammonia obtained by the heating of the reaction solution are subsequently reacted to form urea in a suitable device in accordance with a method known from the prior art.

The technical production of urea from ammonia and carbon dioxide has been known for a long time. In order to provide the educt carbon dioxide, natural gas is commonly burnt for this purpose. This process for providing the educt carbon dioxide has, however, the disadvantage that a valuable energy carrier (natural gas) is used in order to produce a comparatively low value product (carbon dioxide). In this respect, the invention goes down a completely different route—the waste product carbon dioxide which is abundantly present in flue gases from combustion plants is removed from the flue gases with an aqueous ammonia solution and thus rendered usable. It is thus not necessary to burn a valuable energy carrier to provide an educt of the urea synthesis and instead exhaust gases from combustion plants are used for this purpose. This advantageously results in the avoidance of the combustion of a valuable energy carrier and simultaneously or in addition reduces the $CO_2$ level, since at least a portion of the carbon dioxide content of the flue gases is chemically bonded in the form of urea.

It is thus possible with the present invention to convert a considerable portion of the "waste product" carbon dioxide present in flue gases into a valuable material, namely urea. Urea is an important raw material for the bulk chemical industry, which is required in large volumes. The invention thus permits the emission of carbon dioxide to be considerably reduced, whereby this occurs with the conversion of a waste product into a valuable product. This valuable product may be sold so that the method in accordance with the invention may thus be conducted economically as a whole. This synergy effect, on the one hand the reduction of the $CO_2$ emission and on the other hand the conversion of a waste product into a valuable product, renders an economical method possible, which may be used in a large technical scale.

In an advantageous embodiment of the method in accordance with the invention, removing dust and removing nitrogen from the flue gases further includes the removal of sulfur from the flue gases. This is particularly advantageous if the flue gases from the combustion plants contain a high $SO_2$ concentration. As a result of the additional desulfurization step, it is possible to adjust the sulfur dioxide concentration of the flue gas in a controlled manner and thus to influence the concentration of ammonium sulfate in the reaction solution. The method in accordance with the invention is not limited to a particular desulfurization process—all methods known from the prior art can be used.

Modern combustion plants produce considerable volumes of carbon dioxide. Correspondingly large volumes of ammonia are necessary in order to convert at least a portion of the carbon dioxide. The ammonia necessary for the aqueous ammonia solution is advantageously produced on site by ammonia synthesis. The complex and cost-intensive transport and the storage of the ammonia are avoided in this manner and there is always a sufficient amount of ammonia available.

In the method in accordance with the invention, ammonium sulfate is produced in the reaction solution in addition to ammonium carbonate. Ammonium sulfate is an important fertilizer additive and is used in the chemical industry, amongst other things, as a protein precipitant, as a floatation agent for the production of synthetic resin and for manufacturing fire extinguishing powder and flame retardants. Advantage is taken of the fact, that the ammonia sulfate can be separated from the reaction solution after the heating process during which ammonium carbonate decomposes. The separation of the ammonium sulfate can be performed with a spray drying process in a particularly simple and thus advantageous manner.

For the conversion of sulfur dioxide to ammonium sulfate, the sulfur must be oxidized. Air is preferably used as the oxidizing agent. This is available in any desired amount and its handling does not constitute any problem at all.

In known methods of producing urea, an $NH_3/CO_2$ educt ratio of 2.5-4 is used—$NH_3$ is thus used in an excess with respect to $CO_2$. For the purpose of cost reduction and minimization of the necessary amount of ammonia, it is therefore advantageous that the excess ammonia is recirculated for the urea synthesis or for producing the aqueous ammonia solution.

The present invention also provides for an apparatus for cleaning flue gases from a combustion plant with the subsequent production of urea.

The apparatus in accordance with the invention for cleaning flue gases from a combustion plant includes devices for removing nitrogen and removing dust from the flue gases. These directly follow the combustion and can be operated in accordance with methods known from the prior art. The sequence of the devices for the removal of nitrogen and the removal of dust may be as desired.

Downstream of the devices for the removal of nitrogen and the removal of dust is a washing device, in which at least a portion of the flue gases is brought into contact with an aqueous ammonia solution in the presence of an oxidizing agent, whereby a reaction solution forms, which contains at least ammonium carbonate. In addition to ammonium carbonate, the reaction solution also contains ammonium sulfate, which is formed by the reaction of ammonia and sulfur dioxide in the presence of an oxidizing agent.

Downstream of the washing device is a stripper, in which the reaction solution is treated such that the ammonium carbonate contained in the reaction solution decomposes into ammonia and carbon dioxide. In order to achieve such a decomposition, the reaction solution must be heated at normal pressure to above 58° C. The decomposition of ammonium carbonate can be promoted by numerous measures, such as a reduction in pressure.

Downstream of the stripper is a urea plant, in which ammonia and carbon dioxide are reacted to form urea. This reaction can be effected in accordance with methods for urea synthesis known from the prior art.

There are further advantageous embodiments of the apparatus in accordance with the invention.

The method in accordance with the invention and the apparatus in accordance with the invention will be described below with reference to a preferred exemplary embodiment in conjunction with the drawings.

Further areas of applicability of the present invention will become apparent from the detailed description provided hereinafter: It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, which are not necessarily to scale, wherein.

DETAILED DESCRIPTION OF THE INVENTION

Figure 1:
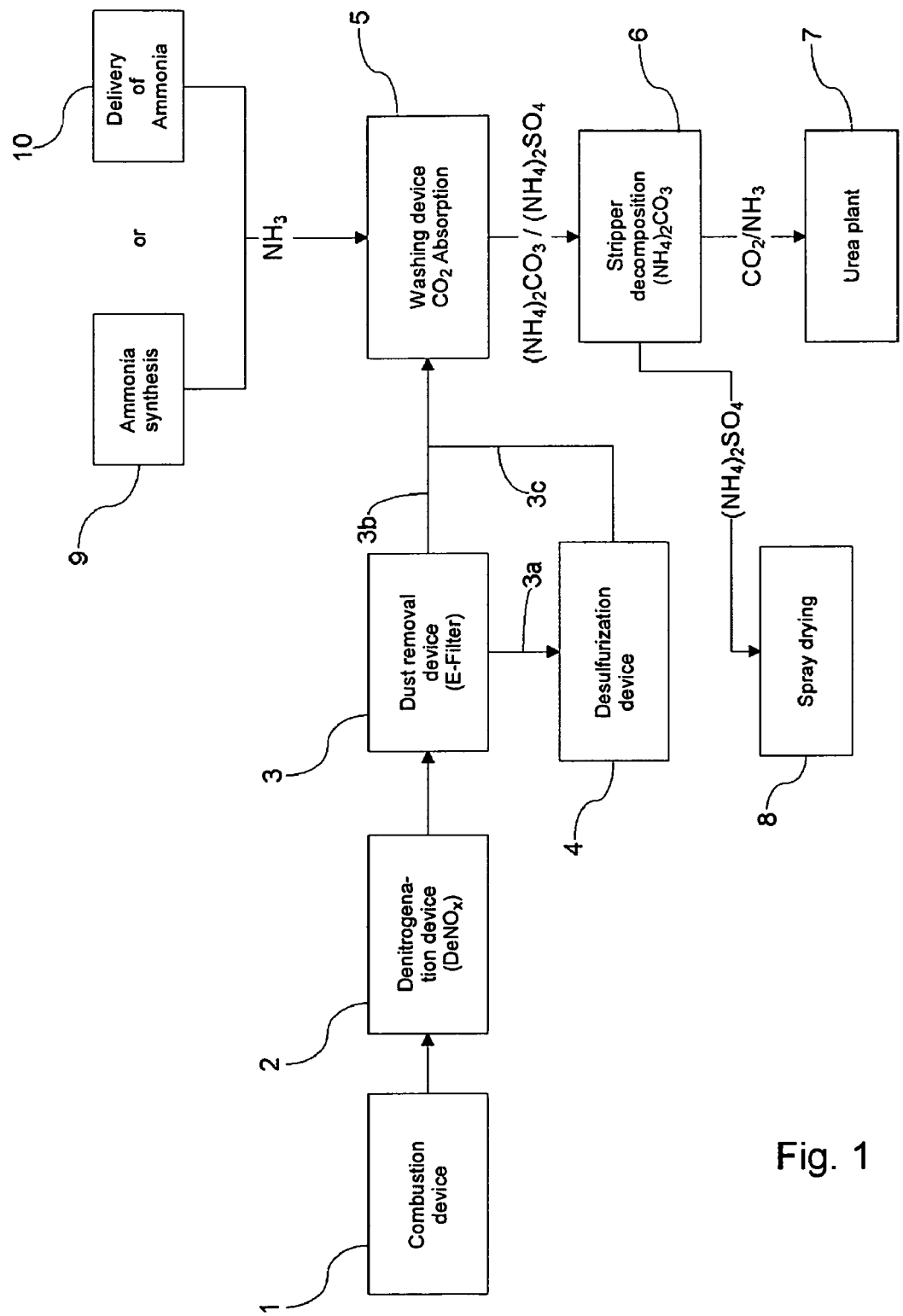
FIG. 1 is a flow process diagram of a preferred embodiment of the method in accordance with the invention and the apparatus in accordance with the invention.

The following detailed description of the embodiment(s) is merely exemplary in nature and is in no way intended to limit the invention, its application, or uses.

The apparatus shown in FIG. 1 includes a combustion plant (1). The contaminated flue gas produced during combustion flows via a conduit into a denitrogenation device (2), in which nitrogen oxides are removed from the flue gas. In the apparatus in accordance with FIG. 1, downstream of the denitrogenation device (2) is a dust removal device (3), in which solid components (ash) are separated from the flue gas flow.

Leading from the dust removal device (3) are conduits (3a, 3b) going to a desulfurization device (4) and a washing device (5), whereby the desulfurization device (3) is in turn connected via a conduit (3c) to the washing device. In such an arrangement of the individual devices, it is possible to pass any desired volumetric portion of the flue gas flow through the desulfurization device. In the event that the flue gas flow only has a low content of sulfur dioxide, the passage through the separate desulfurization device can be omitted. Traces of sulfur dioxide that are present can be removed in the washing device (5).

Downstream of the dust removal device (3) or the desulfurization device (4) is a washing device (5), in which at least a portion of the flue gases is brought into contact with an aqueous ammonia solution. When so brought into contact, carbon dioxide reacts to form ammonium carbonate, whereby a reaction solution containing ammonium carbonate is produced. When the contact process occurs, sulfur dioxide contained in the flue gases also reacts in the presence of an oxidizing agent to form ammonium sulfate, whereby atmospheric oxygen is commonly used as the oxidizing agent. In the event that the atmospheric oxygen content of the flue gases is too low, additional atmospheric oxygen can be supplied. This can be supplied to the flue gas flow before the washing device or directly before or whilst bringing it into contact with the ammonia solution. After the reaction of the flue gases with the ammonia solution, the remaining flue gases are conducted away and, after optional further cleaning steps, discharged to the atmosphere. The ammonia necessary for the production of the aqueous ammonia solution can either be produced in an ammonia synthesis plant (9) on site or delivered and stored in appropriate supply tanks (10) to supply the washing device (5).

The reaction solution forming during the contact process is withdrawn from the washing device (5) and supplied via a conduit to a stripper (6), in which this solution is so treated that the ammonium carbonate contained in it decomposes. This treatment can, for instance, be heating of the reaction solution to >58° C.—above this temperature the ammonium carbonate decomposes into its educts—ammonia and carbon dioxide, which are withdrawn in the form of a rich gas flow and supplied via a conduit to the urea plant (7). In this the ammonia and carbon dioxide are reacted to form urea if necessary with the addition of further ammonia. The urea plant (7) itself can be operated in accordance with any desired process known from the prior art. Excess ammonia is re-circulated and can either be used to produce the aqueous ammonia solution or re-used directly in the urea synthesis.

The reaction solution remaining from the decomposition of ammonium carbonate includes a portion of ammonium sulfate which is dependent on the sulfur dioxide concentration of the flue gases flowing into the washing device (5). In order to render the ammonium sulfate usable, the reaction solution is withdrawn from the stripper and supplied to a spray drying installation (8). An installation for purifying the ammonium sulfate can optionally be connected downstream of the spray drying installation.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements.

The invention claimed is:

1. A method of cleaning flue gases from combustion plants, including the steps of:
   removing dust and removing nitrogen from the flue gases,
   bringing the flue gases into contact with an aqueous ammonia solution in the presence of an oxidizing agent, whereby a reaction solution forms, which contains at least ammonium carbonate,
   heating the reaction solution such that ammonium carbonate decomposes and carbon dioxide and ammonia transfer into the gas atmosphere,
   reacting the gaseous carbon dioxide and the gaseous ammonia to form urea.

2. The method as claimed in claim 1, wherein removing dust and removing nitrogen from the flue gases further comprises the removal of sulfur.

3. The method as claimed in claim 1, wherein the ammonia necessary for the aqueous ammonia solution is produced on site by ammonia synthesis.

4. The method as claimed in claim 1, wherein ammonium sulfate is separated from the reaction solution after heating the reaction solution, during which ammonium carbonate decomposes.

5. The method as claimed in claim 4, wherein the separation of the ammonium sulfate is performed by spray drying.

6. The method as claimed in claim 1, wherein air is used as the oxidizing agent.

7. The method as claimed in claim 1, wherein excess ammonia from reacting the gaseous carbon dioxide and the gaseous ammonia to form urea is re-circulated for the urea synthesis or for producing the aqueous ammonia solution.

* * * * *